United States Patent
Ventur et al.

(10) Patent No.: US 8,887,723 B2
(45) Date of Patent: Nov. 18, 2014

(54) DEVICE FOR FILTERING BREATHING GAS

(75) Inventors: Marco Ventur, Lübeck (DE); Pierre Mühlbauer, Lübeck (DE); Markus Hampe, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 150 days.

(21) Appl. No.: 13/419,897

(22) Filed: Mar. 14, 2012

(65) Prior Publication Data

US 2012/0234318 A1    Sep. 20, 2012

(30) Foreign Application Priority Data

Mar. 15, 2011    (DE) .......................... 10 2011 014 018

(51) Int. Cl.
| | | |
|---|---|---|
| *A61M 11/00* | (2006.01) | |
| *A61M 16/10* | (2006.01) | |
| *A61M 16/20* | (2006.01) | |
| *A61M 16/00* | (2006.01) | |

(52) U.S. Cl.
CPC ......... *A61M 16/1055* (2013.01); *A61M 16/208* (2013.01); *A61M 2205/3666* (2013.01); *A61M 2016/0042* (2013.01); *A61M 2205/362* (2013.01); *A61M 16/1065* (2014.02)
USPC ................. 128/205.12; 128/205.27

(58) Field of Classification Search
CPC . A61M 16/105; A61M 16/208; A61M 16/06; A61M 16/22; A61M 16/10; A61M 2016/0039; A61M 2016/107; B01D 2259/4533; B01D 2256/12
USPC ............. 128/207.14–207.16, 205.12, 203.12, 128/205.27
See application file for complete search history.

(56) References Cited

U.S. PATENT DOCUMENTS

| | | | | |
|---|---|---|---|---|
| 3,707,965 | A | * | 1/1973 | Guzay ...................... 128/205.28 |
| 4,038,051 | A | * | 7/1977 | Ide ................................. 96/408 |
| 4,168,706 | A | * | 9/1979 | Fletcher et al. .......... 128/204.16 |
| 4,232,667 | A | * | 11/1980 | Chalon et al. ............ 128/203.26 |
| 4,657,713 | A |  | 4/1987 | Miller |
| 4,727,871 | A |  | 3/1988 | Smargiassi et al. |
| 4,753,758 | A |  | 6/1988 | Miller |
| 5,131,387 | A | * | 7/1992 | French et al. ............ 128/205.27 |
| 5,143,060 | A |  | 9/1992 | Smith |
| 5,706,799 | A | * | 1/1998 | Imai et al. ................ 128/205.12 |
| 6,105,576 | A | * | 8/2000 | Clawson et al. ......... 128/205.12 |
| 6,415,788 | B1 | * | 7/2002 | Clawson et al. ......... 128/201.13 |
| 6,941,945 | B2 |  | 9/2005 | Flodin |
| 8,176,916 | B2 | * | 5/2012 | Pedarzini et al. ........ 128/205.12 |
| 2001/0029949 | A1 |  | 10/2001 | Blackhurst et al. | |

FOREIGN PATENT DOCUMENTS

| | | |
|---|---|---|
| CN | 18 78 589 A | 12/2006 |
| WO | 2005/047797 A2 | 5/2005 |

* cited by examiner

*Primary Examiner* — Steven Douglas
(74) *Attorney, Agent, or Firm* — McGlew and Tuttle, P.C.

(57) ABSTRACT

A device (FV) for filtering breathing gas has a housing (G) with a gas inlet (GE), a gas outlet (GA) and a filter (F), which is arranged in a first housing section (G1) formed between the gas inlet (GE) and the gas outlet (GA). The housing (G) has a second housing section (G2) gas-tightly separated from the first housing section (G1) with at least one first wall (W1, W2, W3), which establishes a thermal contact with a wall (W1, W2, W3) of the first housing section (G1). The second housing section (G2) has an opening on an outer side of the housing (G).

19 Claims, 4 Drawing Sheets

NEW SHEET

DEVICE FOR FILTERING BREATHING GAS

CROSS REFERENCE TO RELATED APPLICATIONS

This application claims the benefit of priority under 35 U.S.C. §119 of German Patent Application DE 10 2011 014 018.2 filed Mar. 15, 2011, the entire contents of which are incorporated herein by reference.

FIELD OF THE INVENTION

The present invention pertains to a device for filtering breathing gas.

BACKGROUND OF THE INVENTION

Respiration systems are usually used for medical applications to support breathing and/or to administer anesthetics during surgical procedures. While the breathing gas circulates in a closed circuit in anesthesia systems and is fed again to the patient after the carbon dioxide contained in the expired air has been removed in a carbon dioxide absorber, an open circuit is usually used in respiration systems in intensive care, i.e., the expired air is fed to the room air. Bacteria filters are used to maintain the breathing gas flowing in respiration systems germ-free. Furthermore, devices for enriching the breathing gas with moisture may be present in respiration systems in order to bring about moistening of the patient's airways. Bacteria filters may be arranged on both the inspiration side and the expiration side of the breathing circuit.

Condensation may occur due to moisture present in the breathing gas because of active moistening and/or due to the moisture present due to expiration by a patient. Condensation in the bacteria filter leads to moistening of the filter material and it brings about, as a result, a reduction of the permeability to air of the filter over time, because the filter resistance increases. This compromises the patient's ability to breath and leads to the need to replace bacteria filters more often than it would be necessary based on contamination by bacteria alone.

An electric heating element, by means of which the filter is heated, is used, for example in U.S. Pat. No. 4,727,871 to prevent condensation in an antibacterial filter. The heating elements used for this and the means necessary for operation for controlling and for supplying the heating elements with power make the manufacture of such a filter complicated and expensive.

Instead of an active heating of a filter or of a filter housing surrounding the filter, another housing is arranged around the filter housing in US 2001/0029949A1, so that an air gap is formed between the filter housing and the additional housing. The condensation within the filter housing shall be reduced by the insulating action of the air gap. However, the insulating action of such an air gap is limited, so that long-term use for more than one day is not possible with such filters.

SUMMARY OF THE INVENTION

A basic object of the present invention is to provide an advantageous device for filtering breathing gas with improved service life of the filter, which makes do without electric heating elements arranged directly at the filter or at the filter housing.

According to the invention, a device for filtering breathing gas is provided. The device comprises a housing with a gas inlet and a gas outlet and having a first housing section formed between the gas inlet and the gas outlet and a second housing section gas-tightly separated from the first housing section. The first housing section has a first housing section wall surface. The second housing section has a second housing section wall surface establishing thermal contact with the first housing section wall surface. The second housing section has an opening on an outer side of the housing. A filter is arranged in the first housing section.

The device may further comprise a connection line wherein the gas outlet and the opening of the second housing section are connected via the connection line. A valve with an outlet arranged in the connection line may be provided so that breathing gas flows into the second housing section through both the outlet and the opening.

The first housing section wall surface and said second housing section wall surface may be opposite wall surfaces of a common wall.

According to another aspect of the invention, a respiration system is provided comprising a device for providing breathing gas with an outer wall and the device for filtering breathing gas. At least one outer wall of the second housing section is arranged adjacent to the outer wall of the device for providing breathing gas, which outer wall of the device for providing breathing gas is formed in a recess, such that air flowing past in the recess at the outer wall of the device for providing breathing gas also flows along the at least one outer wall of the second housing section.

The device according to the present invention for filtering breathing gas has a housing with a gas inlet, a gas outlet and a filter, which is arranged in a first housing section formed between the gas inlet and the gas outlet, wherein the housing has a second housing section gas-tightly separated from the first housing section, with at least one first wall, which establishes a thermal contact with a wall of the first housing section. The second housing section has an opening according to the present invention on an outer side of the housing.

Heated gas can be introduced into the volume of the second housing section, so that the first housing section and hence also the filter are heated by the thermal contact between the first housing section and the second housing section. For example, the gas introduced into the volume of the second housing section via the opening may be breathing gas heated downstream of the filter or heated waste air of a device used to provide the breathing gas. The temperature of the gas introduced can be selected to be such that the device can be used for more than 24 hours before the resistance of the filter, which is increasing continuously during the operation because of a remaining residual condensation, reaches a value that requires replacement thereof in order to make it possible to continue ensuring proper respiration of the patient.

The housing may be made, in principle, of either metal or plastic. However, the housing is preferably manufactured from polypropylene (PP).

The gas outlet and the opening of the second housing section are advantageously connected via a connection line.

The breathing gas flowing in the connection line can be heated in this manner, for example, by a warm air stream flowing past at the connection line such that that heated breathing gas enters the volume of the second housing section. The connection line may be connected detachably to the gas outlet and the opening, for example, by bonding or ultrasonic welding. The connection line and the housing may, of course, also be made in one piece.

A valve with an outlet is arranged in the connection line in a preferred embodiment, so that breathing gas flows through the outlet as well as through the opening into the second housing section with the valve opened.

If the device is used, for example, with a respirator on the expiration side of a breathing circuit, an expiration valve is usually present downstream of the filter in order to control the breathing circuit. The expiration valve may be arranged adjacent to the respirator, so that means for heating air and allowing it to flow over the expiration valve may be provided at the respirator. This warm air stream, which can also be used at the same time to heat a sensor arranged at the outlet of the valve for measuring the breathing gas flow, heats the breathing gas flowing through the valve, so that, on the one hand, the breathing gas leaves the outlet in an already heated state in the direction of the sensor and, on the other hand, heated breathing gas is sent through the opening into the second housing section.

In a respiration system with a device according to the present invention, at least one outer wall of the second housing section is arranged advantageously adjacent to an outer wall of a device for providing breathing gas. The outer wall of the second housing section is provided in a recess, in such a way that air flowing past the outer wall of the device in the recess also flows past the outer wall of the second housing section. The breathing gas present in the volume of the second housing section can be additionally heated in this manner by heated air being sent past the outer wall of the device and hence also past the outer wall of the second housing section.

The distance between the outer wall of the device and the outer wall of the second housing section is advantageously between 0.5 mm, and 5 mm.

The present invention will be explained in more detail below on the basis of an exemplary embodiment shown in the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
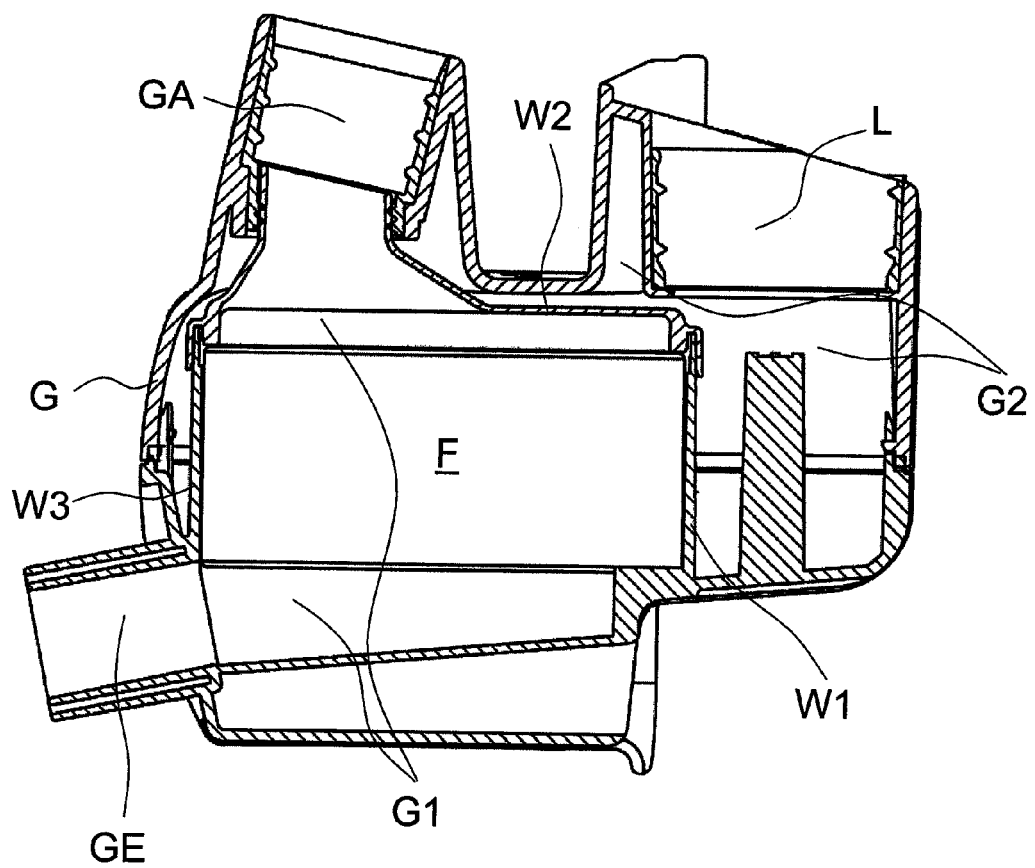
FIG. 1 is a sectional view showing a device according to the present invention for filtering breathing gas.

Referring to the drawings in particular, identical reference numbers in the figures designate identical objects.

FIG. 1 schematically shows a section through a device FV for filtering breathing gas. Device FV has a housing G with a first housing section G1 and with a second housing section G2. Breathing gas can enter the first housing section G1 via a gas inlet GE. The breathing gas can enter the gas outlet GA via a bacteria filter F arranged in the first housing section G1 and leave the first housing section G1 there. The first housing section G1 is of a gas-tight design within housing G and is partly surrounded by the second housing section G2. Gas-tight within the housing G is defined such that the first housing section G1 has no openings located within the housing, through which breathing gas could enter the second housing section G2.

The second housing section G2 is defined by outer walls of housing G and by walls W1, W2, W3 of the first housing section G1, so that a hollow space is formed by the second housing section G2 between the outer walls of housing G and walls W1, W2, W3 of the first housing section G1. Due to the fact walls W1, W2, W3 defining the first housing section G1 are also walls defining the second housing section G2 at the same time, there is a thermal contact between the first housing section G1 and the second housing section G2. The first housing section G1 and the second housing section G2 may, of course, also have separate walls in an alternative embodiment, but these walls adjoin each other directly and establish a thermal contact as a result.

The second housing section G2 has, furthermore, an opening L on an outer side of housing G. Heated gas can be introduced via opening L into the second housing section G2. The introduction of heated gas may take place, for example, via a line connected to the gas outlet GA, which line is not shown in FIG. 1 and which passes on the breathing gas in the breathing circuit and additionally also has a connection to opening L. If, for example, warm air flows around this line or this line is heated by a heating element, heated breathing gas enters the second housing section G2. Due to the heating resulting herefrom of both the first housing section G1 and the bacteria filter F arranged therein, the condensation at the bacteria filter G can be reduced in such a way that, as a result, the breathing resistance only becomes high enough to make a filter change necessary after 2 to 5 days.

Figure 2:
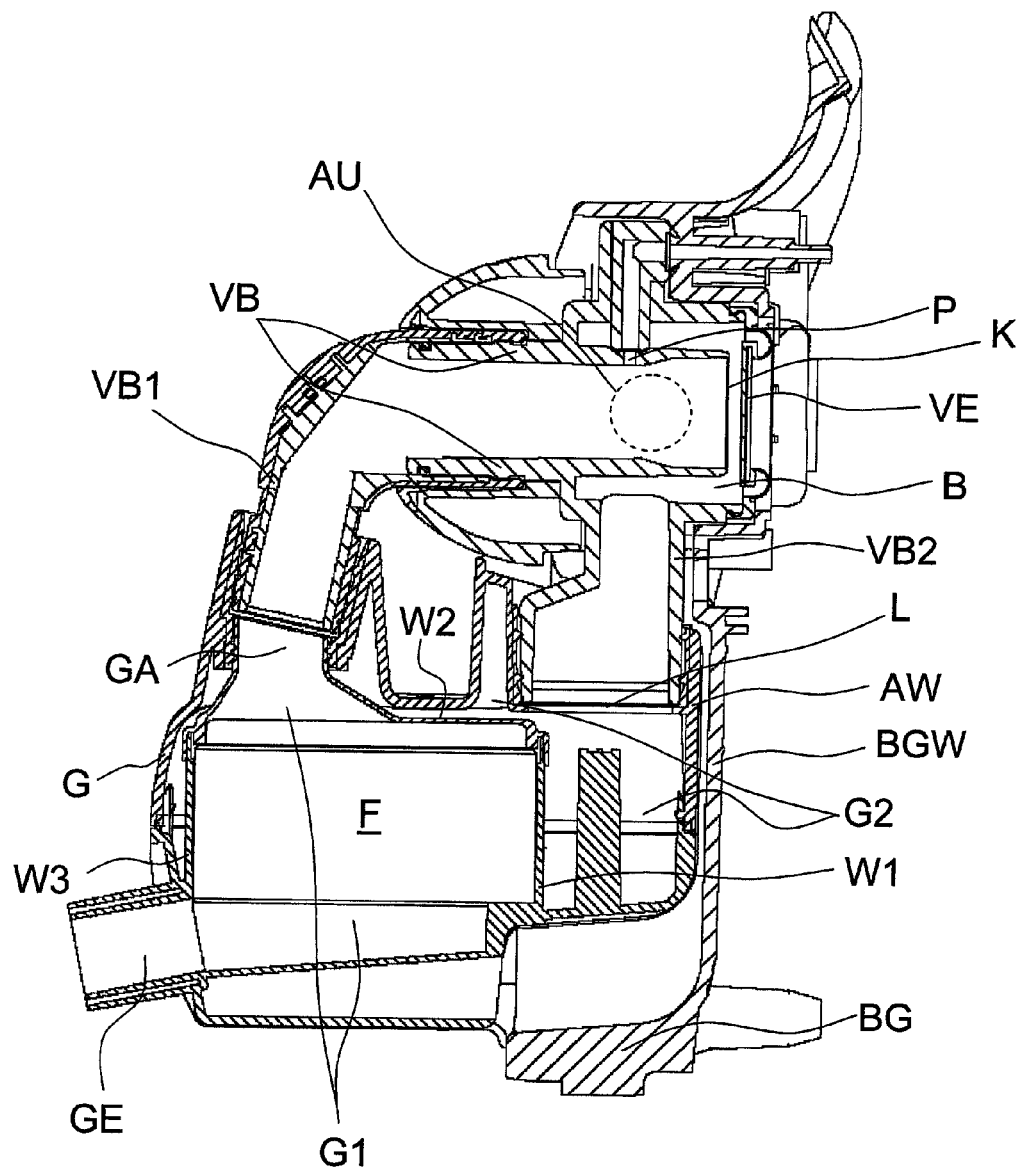
FIG. 2 is a sectional view showing a device according to FIG. 1 with a connection line with a valve between a gas outlet and an opening in the housing of the device.

FIG. 2 schematically shows the device FV according to FIG. 1 in the same section plane. Device FV is fastened, for example, to a respirator BG with fastening means, not shown, and is located on the expiration side of the breathing circuit. Breathing gas enters the device FV via gas inlet GE. The breathing gas was enriched with moisture before on the inspiration side, not shown, of the breathing circuit and/or by a patient's respiratory activity. The moist breathing gas passes through the bacteria filter F, which is arranged within the first housing section G1, and leaves housing G via gas outlet GA. Gas outlet GA is in turn connected via a first section VB1 of a connection line VB with an expiration valve VE. Expiration valve VE is designed, for example, as a membrane, which is pressed against valve opening K to close expiration valve VE. The patient's breathing is controlled by means of expiration valve VE and breathing gas enters the room air via an outlet AU formed at expiration valve VE when expiration valve VE is opened. The outlet is behind the drawing plane in FIG. 2. This is indicated by broken lines. As an alternative, outlet AU may also be connected to a suction device to draw off the breathing gas.

After the breathing gas has passed through the closing mechanism of expiration valve VE, it not only enters the room air via outlet AU, but also a second section VB2 of connection line VB from expiration valve VE via area B and from there it enters the second housing section G2 via opening L.

Connection line VB may be detachably connected to gas outlet GA and opening L, for example, by a gas-tightly clamping plug-type connector or nondetachably, for example, by bonding or ultrasonic welding. Connection line VB may, of course, also be made in one piece with housing G.

Furthermore, an opening P, via which a connection is established with a pressure sensor arranged in the respirator, is formed in connection line VB.

Figure 3:
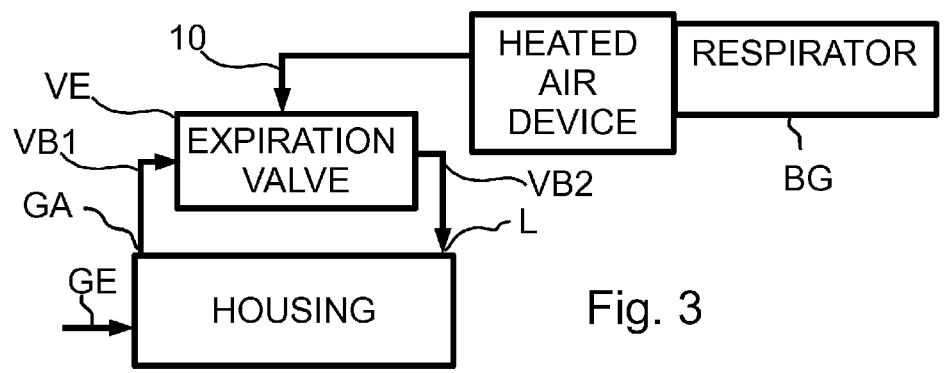
FIG. 3 is a schematic view of a device according to FIG. 1, with the device heated with the air from a respirator.

A heated air device, shown in FIG. 3, by means of which heated air is sent to the expiration valve VE, is formed at and/or in respirator BG. For example, a heating element, which heats air in respirator BG, may be present in respirator BG. The heated air can be sent to the expiration valve by means of a blower and, for example, elements 10 for guiding the air stream, which are provided at and/or in the respirator BG. The breathing gas flowing through the expiration valve VE is heated hereby and condensation takes place only after the closing mechanism of expiration valve VE. The condensed water enters, just as the heated breathing gas, the second housing section G2, which is thus also used as a water trap, via the second section VB2 of connection line VB.

The heated air stream can be additionally guided such that it also flows past an outer wall AW of the second housing section G2 and heats outer wall AW. To let the heated air flow past the outer wall AW, respirator BG has a recess, within which at least the outer wall AW of the second housing section G2 is arranged. The outer wall AW of the second housing section G2 is arranged in the recess adjacent to an outer wall BGW of respirator BG such that a heated air stream sent past the outer wall BGW of the respirator BG also must flow past the outer wall AW of the second housing section G2 and heats same as a result. The distance between outer wall BGW of respirator BG and the outer wall AW of the second housing section G2 is approx. 1 mm in this exemplary embodiment. A distance of between 0.5 mm and 5 mm is preferably selected in order to bring about sufficient heat exchange between the heated air flowing through and the outer wall AW of the second housing section G2.

Furthermore, the waste air of the respirator BG, which air is heated by the operation, is sent to the expiration valve VE and to the outer wall AW of the second housing section G2, for example, through slots, not shown, in the housing of the respirator BG and optionally supported by a blower, not shown, so that both the expiration valve VE and the outer wall AW of the second housing section G2 are additionally heated by the heated waste air of respirator BG.

Expiration valve VE may, of course, also be arranged within respirator BG. In this case, not shown in the figures, the gas outlet GA is connected by means of a connection line to an inlet leading to the expiration valve arranged in respirator BG, and a connection is branched off to opening L from the connection line in front of this inlet, for example, by means of a T-piece. This connection line is heated by the flowing past of heated air in the same manner as this was described before on the basis of FIG. 2 for the expiration valve VE arranged outside the housing of the respirator, so that heated breathing gas will likewise enter the second housing section G2.

Figure 4:
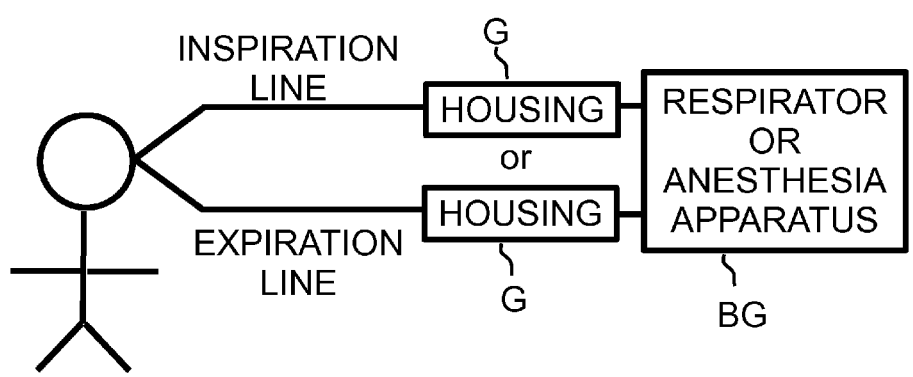
FIG. 4 is a schematic view of a breathing circuit with a device according to FIG. 1 arranged in either an inspiration side or an expiration side of the breathing circuit.

The device according to the present invention for filtering breathing gas is preferably used combined with a respirator in intensive care, as shown in FIG. 4. This device may, of course, also be used in a closed breathing circuit of an anesthesia apparatus. The device according to the present invention is preferably used on the expiration side of a breathing circuit. However, use on the inspiration side is also possible, in principle.

Figure 5:
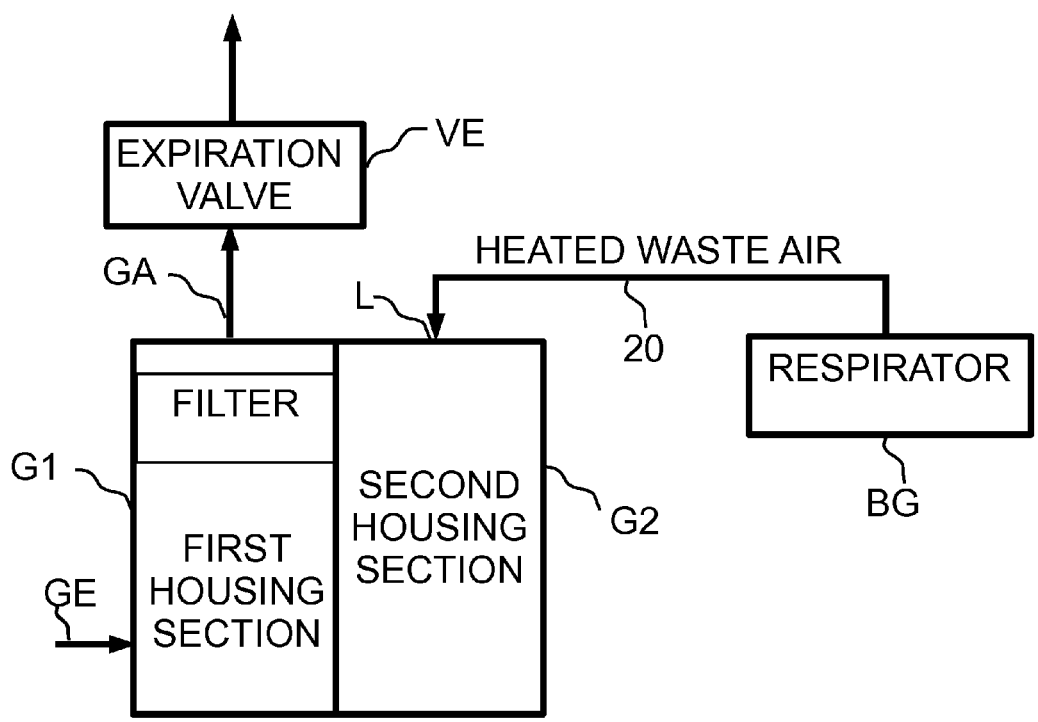
FIG. 5 is a schematic view of a device according to FIG. 1 heated with the air from a respirator in another embodiment.

In one exemplary embodiment, shown in FIG. 5, the gas outlet GA of the device FV for filtering breathing gas is likewise connected via a connection line to an expiration valve, similarly to the view in FIG. 2. However, a connection between the expiration valve and opening L is eliminated in this exemplary embodiment. To bring about heating of the first housing section G1 and of the bacteria filter F, heated waste air of a respirator BG is fed to the second housing section G2, for example, via a flexible tube 20 connected to opening L.

While specific embodiments of the invention have been shown and described in detail to illustrate the application of the principles of the invention, it will be understood that the invention may be embodied otherwise without departing from such principles.

APPENDIX

List of Reference Numbers

AU Outlet of expiration valve
AW Outer wall of second housing section
BG Respirator
BGW Outer wall of respirator
F Bacteria filter
G Housing
G1 First housing section
G2 Second housing section
GE Gas inlet
GA Gas outlet
K Opening closable by expiration valve
L Opening in second housing section
P Opening for pressure measurement
VB Connection line
VB1 First section of connection line
VB2 Second section of connection line
VE Expiration valve
W1 Wall
W2 Wall
W3 Wall

What is claimed is:

1. A device for filtering breathing gas, the device comprising:
   a housing with a gas inlet and a gas outlet and having a first housing section formed between said gas inlet and said gas outlet, said first housing section having a first housing section wall surface, said housing having a second housing section completely gas-tightly separated from said first housing section inside of said housing, said second housing section having a second housing section wall surface in thermal contact with said first housing section wall surface, said second housing section having an opening on an outer side of said housing; and
   a filter arranged in said first housing section.

2. A device in accordance with claim 1, further comprising a connection line wherein said gas outlet and said opening of said second housing section are connected via said connection line.

3. A device in accordance with claim 2, further comprising a valve with an outlet arranged in said connection line so that breathing gas flows into said second housing section through both said outlet and said opening.

4. A device in accordance with claim 1, wherein said first housing section wall surface and said second housing section wall surface are opposite wall surfaces of a common wall.

5. A respiration system comprising:
   a device for providing breathing gas, which device has an outer wall;
   a filtering device comprising a housing with a gas inlet and a gas outlet and having a first housing section formed between said gas inlet and said gas outlet, said first housing section having a first housing section wall surface, said housing having a second housing section completely gas-tightly separated from said first housing section between said gas inlet and said gas outlet, said second housing section having a second housing section wall surface in thermal contact with said first housing section wall surface, said second housing section having an opening from an interior of said second housing section to an outer side of said housing and a filter arranged in said first housing section, wherein at least one outer wall of said second housing section is arranged adjacent to said outer wall of said device for providing breathing gas, which said outer wall of said device for providing breathing gas is formed in a recess, such that air flowing past in the recess at said outer wall of said device for providing breathing gas also flows along said at least one outer wall of said second housing section.

6. A respiration system in accordance with claim 5, further comprising a connection line wherein said gas outlet and said opening of said second housing section are connected via said connection line.

7. A respiration system in accordance with claim 6, further comprising a valve with an outlet arranged in said connection line so that breathing gas flows into said second housing section through both said outlet and said opening.

8. A respiration system in accordance with claim 5, wherein said first housing section wall surface and said second housing section wall surface are opposite wall surfaces of a common wall.

9. A respiration system in accordance with claim 5, wherein said second housing section is in thermal contact with said first housing section via said first housing section wall surface and said second housing section wall surface that are opposite wall surfaces of a common wall.

10. A device in accordance with claim 1, further comprising:
a heated air device feeding heated air to said opening of said second housing section, said heated air device providing the heated air as one of heated breathing gas and heated air from a device used to provide respiratory gas.

11. A respiration system for a patient, the respiration system comprising:
an inspiration side feeding breathing gas to the patient;
an expiration side connected to said inspiration side, and removing the breathing gas from the patient;
a housing arranged in line in one of said inspiration and expiration sides, said housing having an inlet arranged to receive the breathing gas from an upstream portion of said one of said inspiration and expiration side, said housing having an outlet arranged to feed the breathing gas out from said housing and into a downstream portion of said one of said inspiration and expiration sides;
a first housing section positioned in said housing and arranged to guide the breathing gas from said inlet of said housing, through said first housing section, and then out through said outlet of said housing;
a filter arranged in said first housing section, and filtering the breathing air passing through said first housing section; and
a second housing section arranged in said housing, said housing and said second housing section together having an outer side defining an opening, said second housing section and said first housing section having a barrier completely gas-tightly separating said first housing section from said second housing section upstream of said outlet, said barrier includes a common wall of said first and second housing, said common wall having one side defining an interior space of said first housing section, said common wall having another side defining an interior space of said second housing section, said one side and said another side of said common wall being on diametrically opposite sides of said common wall.

12. A respiration system in accordance with claim 11, further comprising:
a connection line providing a flow path between said gas outlet of said housing and opening of said housing and second housing section.

13. A respiration system in accordance with claim 12, further comprising:
an expiration valve positioned in said connection line, said expiration valve including a valve opening and a membrane biased against said valve opening, said expiration valve being arranged to control the patients breathing, said expiration valve and said connection line being arranged to flow the breathing gas through both said expiration valve and said opening and then into said second housing section.

14. A respiration system in accordance with claim 12, further comprising:
a heated air device feeding heated air to said connection line and arranged to heat the breathing gas flowing through the connection line;
said connection line, said heated air device and said second housing section being arranged to flow the heated breathing gas from said connection line into said second housing section.

15. A respiration system in accordance with claim 13, further comprising:
a heated air device feeding heated air to said expiration valve and arranged to heat the breathing gas flowing through the expiration valve;
said connection line, said heated air device and said second housing section being arranged to flow the heated breathing gas from said expiration valve into said connection line and into said second housing section.

16. A respiration system in accordance with claim 12, further comprising:
one of a respirator and anesthesia apparatus connected to one of said inspiration and expiration side of the respiration system.

17. A respiration system in accordance with claim 12, wherein:
a respirator is connected to one of said inspiration and expiration side of the respiration system, said respirator having an outer wall, said respirator generating a heated air stream along said outer wall of said respirator;
said second housing section includes an outer wall located along the heated air stream of said respirator to cause said outer wall of said second housing section to be heated by the heated air stream.

18. A respiration system in accordance with claim 16, wherein:
said outer wall of said respirator and said outer wall of said second housing section defines a flow path for the heated air stream of said respirator, said outer wall of said respirator and said second housing section being on diametrically opposite sides of said flow path for the heated air stream.

19. A respiration system in accordance with claim 11, further comprising:
a respirator connected to one of said inspiration and expiration side of the respiration system, said respirator generating heated waste air;
a tube feeding the heated waste air from said respirator to said opening of said second housing section and into said second housing.

* * * * *